(12) United States Patent
Kanesaka

(10) Patent No.: US 6,521,244 B1
(45) Date of Patent: Feb. 18, 2003

(54) BODY FILLING MATERIAL

(76) Inventor: Nozomu Kanesaka, 81 Greenwoods Rd., Old Tappan, NJ (US) 07675

(*) Notice: Subject to any disclaimer, the term of this patent is extended or adjusted under 35 U.S.C. 154(b) by 35 days.

(21) Appl. No.: 09/592,919

(22) Filed: Jun. 13, 2000

(51) Int. Cl.⁷ .................... A61K 9/14; A61K 35/34
(52) U.S. Cl. ............... 424/422; 424/423; 424/484; 424/489; 424/492; 424/569; 530/350; 530/353; 514/12; 514/21
(58) Field of Search ................ 424/422, 423, 424/484, 489, 492, 569; 530/350, 353; 514/21, 12

(56) References Cited

U.S. PATENT DOCUMENTS

| | | | | | |
|---|---|---|---|---|---|
| 5,352,715 A | * | 10/1994 | Wallace | ...... | 523/115 |
| 5,972,366 A | * | 10/1999 | Haynes | ...... | 424/422 |
| 6,013,856 A | * | 1/2000 | Tucker | ...... | 623/16 |
| 6,083,522 A | * | 4/2000 | Chu | ...... | 424/423 |
| 6,110,484 A | * | 8/2000 | Sierra | ...... | 424/426 |
| 6,165,490 A | * | 12/2000 | Federov | ...... | 424/427 |
| 6,180,605 B1 | * | 1/2001 | Chen | ...... | 514/12 |
| 6,227,397 B1 | * | 8/2001 | Shimizu | ...... | 424/443 |

FOREIGN PATENT DOCUMENTS

WO        9745147      * 12/1997

* cited by examiner

Primary Examiner—Christopher S. F. Low
Assistant Examiner—David Lukton
(74) Attorney, Agent, or Firm—Kanesaka & Takeuchi

(57) ABSTRACT

A body filling agent is formed of a collagen in the form of powder, fiber or gel, and at least one kind of implantable particles selected from a group consisting of implantable polymer and pericardium. A mixture of the collagen and the implantable particles forming the body filling agent is deposited in a body. The collagen is absorbed into the body, but the implantable particles remain in the body as a part of the body.

2 Claims, No Drawings

BODY FILLING MATERIAL

BACKGROUND OF THE INVENTION AND RELATED ART STATEMENT

The present invention relates to a body filling material or agent for medical purpose.

A body filler is used for various medical purposes, such as cosmetic surgery for stretching facial wrinkles, breast implantation, treatment for incontinent by narrowing urethra, by injecting collagen, and so on. Also, an embolic agent is used for filling a void inside a body, such as treatment of aneurysm in brain and so on. The body filling agent in the present invention is used as the body filler and embolic agent.

One of the most common body fillers used in a medical field is a collagen well known in the art. The collagen is produced from animals, and is very biocompatible with a human body. However, the human body gradually absorbs the collagen, for example in about 6 to 12 months, when applied to the human body. Therefore, if the collagen is used as a permanent body filler, repeated applications of the collagen are required.

Another well-known body filler is silicone. However, due to the problem occurred in the breast implantation, silicone is not used commonly any longer.

It is very important that the body filler is biocompatible for a long term implantation and very easy in application, such as having fluidity. Also, the body filler should not be absorbed into the body too much even if it is absorbed. Preferably, an amount of the body filler to be absorbed into the body is controllable depending on a purpose of use.

Thus, it is desired to provide a body filling agent including a body filler and embolic agent for medical purpose, which is compatible with a human body and can remain at a predetermined position of the body for a long time.

Accordingly, an object of the invention is to provide a body filling agent which is biocompatible to a human body and is used aa a body filler and an embolic agent.

Another object of the invention is to provide a body filling agent as stated above, wherein a desired amount of the body filling agent can remain at a desired position applied in the body for a long time.

Further objects and advantages of the invention will be apparent from the following description of the invention.

SUMMARY OF THE INVENTION

A body filling agent of the invention is formed of a collagen, and at least one kind of implantable particles selected from a group consisting of implantable polymer and pericardium. A mixture of the collagen and the implantable particles form the body filling agent to be deposited in a human body.

The collagen has been known and widely accepted as a filler though the collagen is absorbed into a body in a certain period of time and forms, when mixed with a blood, a blood clot for preventing bleeding. In the invention, the collagen known in the art is used in a powder, fiber or gel form. In view of handling, the collagen in a powder form is used.

The implantable particles used in the present invention are implantable polymer particles, and/or pericardium particles. Namely, the polymer particles and/or pericardium particles in a powder or fibrous form are used.

The implantable polymer may be polyester, urethan and polytetrafluoroethylene. The polymer has been used to form a vein graft to be implanted into the body. In one example, fibers are formed from the polymer and the vein graft is made by weaving the fibers of the polymer. In another example, the polymer is foamed, such as expanded polytetrafluoroethylene, to have an elongated and flexible tube.

In the invention, the polymer used for forming an article for implantation is used. The polymer is processed to form a powder or fiber to be mixed with the collagen. The powder and fibers should have a size to be injectable by an injector.

The pericardium is a membrane tissue surrounding a heart and available from animals, such as pig and cow. The pericardium has been used for implantation, such as soft heart valves and ligaments, and is generally regarded as being compatible with a human body. However, if the pericardium powder is only implanted or applied into a human body as a filler, the pericardium powder is not accepted.

It has been found that although the polymer particles and pericardium particles are not accepted in the human body as body fillers by themselves, the mixture of the collagen and the polymer particles and/or pericardium particles is not rejected and accepted by the human body. Thus, the present invention has been made.

When the mixture of the collagen, and the polymer particles and/or pericardium particles is implanted or applied into the human body, the collagen is gradually absorbed into the body, but the polymer particles and/or pericardium particles remain and accepted in the body. Thus, the mixture can be used as a permanent body filling agent.

The body filling agent is preferably mixed with a suspending liquid, i.e. water, for suspending the mixture of the collagen and the polymer particles and/or pericardium particles. As a result, the body filling agent with the suspending liquid can be injected into the body by an injector, so that the implantation or application of the body filling agent can be made easily.

In preparing the body filling agent of the invention, the polymer as explained above is processed to form a powder or fibers. In case of using the pericardium, the pericardium is obtained from an animal, such as pig or cow, and the pericardium is crushed into a fine powder. The pericardium in the fibrous form may be used. The polymer and/or pericardium particles, i.e. powder or fibers, are mixed with a collagen, i.e. powder, fiber or gel form. When the body filling agent in a fluid form is required, suitable liquid, such as water, is added to the mixture, so that the fluid containing the polymer and/or pericardium particles, and collagen can be injected into a desired place, such as under skin or in muscle by an injector.

DETAILED DESCRIPTION OF PREFERRED EMBODIMENTS

Hereinafter, embodiments of the invention will be explained in detail.

A body filling agent of the invention is used as a body filler and an embolic agent. As the body filler, it can be used for various medical purposes, such as cosmetic surgery for stretching facial wrinkles, breast implantation, and treatment for incontinent by narrowing urethra. As the embolic agent, it can be used for filling a void inside a body, such as treatment of aneurysm in brain and so on.

The body filling agent of the invention is formed of collagen in the form of powder, fiber or gel, and implantable particles, i.e. polymer and/or pericardium particles, which are mixed together. The mixture is applied into a required portion of the body as a body filling agent. The collagen is absorbed gradually, but the implantable particles remain in the body as a substance filled in the body.

The collagen used in the body filling agent of the invention is known in the art. If the obtained collagen is not in the proper powder form, the collagen is crushed into the fine powder in the appropriate method. The collagen in the fiber or gel form may be used. There is no other special requirement.

The implantable particles used in the present invention are implantable polymer particles, and/or pericardium particles. The polymer particles in a powder or short fibers are used.

The implantable polymer may be polyester, urethan and polytetrafluoroethylene, which have been used to form a vein graft to be implanted into a human body. In the invention, these polymers used to form an article implantable in the human body are processed to form a powder or fibers to be mixed with the collagen. There is no special limitation for the powder or fibers as long as the powder and fibers can be well mixed with collagen and can be injected by an injector. In case of a fiber, preferably, the diameter may be 100–300 $\mu$m and the length is 1–2 mm.

In preparing pericardium particles, i.e. powder or fibers, a tissue of the pericardium is used. The pericardium is a membrane tissue surrounding a heart and available from animals, such as pig and cow. Once it is processed by glutaraldehyde, it becomes biocompatible and strong. Conventionally, it is used for a number of implantation, such as soft heart valves, artificial ligaments, and other implantable parts.

In using a pericardium as the body filling agent, firstly, a pericardium of an animal, such as pig and cow, is obtained from a commercial slaughter house. The pericardium is retained in a cold buffer solution and is rapidly shipped to a manufacturer to be processed immediately upon receipt at the manufacturer.

At the manufacturer, the pericardium is rinsed and cleaned in a cold buffered saline to remove foreign substances, such as blood, tissue debris, and fat adhered thereto, and then kept submersed in a container including 2% benzyl alcohol to sterilize the pericardium. The pericardium is inspected to find out if there is a damaged portion, and if a damaged portion is found or observed, it is cut and discarded. The pericardium in the shape of a sac is trimmed so that it will lay flat on a surface. Accordingly, the tissue of the pericardium is ready for a fixation or cross-linkage step.

Then, the pericardium is placed in a shallow container containing fleshly prepared 0.35% glutaraldehyde, or formaldehyde. Then, the pericardium is fixed or crosslinked at a room temperature, and unstressed for a week. Then, the pericardium is transferred to be quarantined for a quality control.

As a quality control of the body filling agent, a shrink temperature test of the tissue of the pericardium is performed to assure a completeness of the fixation or cross-linkage. Shrink temperature ranges from 83 to 87° C., that is, ±85° C. This quality control test need not be made for all pericardia, and a sample picked up from the pericardia may be tested.

Then, the tissue of the pericardium in the sac shape is ready for being crushed into a fine powder. As a method of crushing the pericardium into the powder, quickly freezing the pericardium is very effective. For example, the pericardium is placed in a liquid nitrogen, and quickly frozen. When the tissue of the pericardium is quickly frozen, the tissue is easily crushed into a fine powder. The pericardium in the fibrous form may be used as well. Then, a paste is made from the powder of the tissue of the pericardium using a sterile saline.

Then, the paste of the powder of the tissue is kept in a solution containing alcohol or the like for sterilization to thereby form the powder of the pericardium. The sample of the paste may be quarantined again for a sterility testing.

Incidentally, all the solutions, such as glutaraldehyde, formaldehyde or the like, used for sterilization and fixation must be checked for concentration and pH (7.4±0.05).

The pericardium powder or particles prepared as described above and/or the polymer particles are mixed with the collagen and water to form the body filling agent in a liquid suspension form. An amount of the pericardium and/or polymer particles relative to the collagen is between 20 and 90% by weight. The amount varies depending on the purpose of applying the body filling agent or the place to which the body filling agent is applied.

The body filling agent formed as described above is applied to the desired position in the body, such as under skin or muscle, or the like, by injection.

The mixture of the collagen and polymer and/or pericardium particles in the present invention is acceptable to the body without rejection. Water mixed with the collagen and polymer and/or pericardium particles is absorbed in the body very quickly, i.e. within one or two days. As time passes by, i.e. 6–12 months, the collagen powder in the body filling agent is absorbed by the body, and only the pericardium and/or polymer particles remain as it is in the body to function as the filling agent. Thus, there is no need for repeatedly applying the body filling agent.

When only the pericardium or polymer particles are applied in the body as the body filling agent, the body may reject the pericardium and/or polymer particles. However, as in the embodiment of the invention, when the pericardium and/or polymer particles are mixed with the collagen to form the body filling agent, the mixture is not rejected by the body. Although the collagen is gradually absorbed in the body and only the pericardium and/or polymer particles remain in the body, the pericardium and/or polymer particles are not rejected. Thus, the mixture of the collagen and pericardium and/or polymer particles in the present embodiment is very biocompatible and gives no harm to the body when the pericardium and/or polymer particles remain at the predetermined position of the body for a long term as described above.

The particles of the pericardium and the collagen do not stick to each other nor are solidified after the body filling agent is injected into the body. Also, after the collagen is absorbed into the body, the pericardium particles do no stick or adhere to each other. The mixture of the pericardium particles and the collagen has elasticity, and also the pericardium particles has slight elasticity. Thus, the body filling agent according to the present invention is suitable for medical applications to parts of the body requiring the elasticity, such as the breast implant, a cosmetic surgery for stretching the facial wrinkles, or the like.

The polymer particles may stick to each other in the body. Thus, the mixture of the polymer particles and collagen may be used for a portion which need not require elasticity.

The pericardium and polymer particles remained in the body are covered by the tissues surrounding the same. The body filling agent does not flow to the other parts of the body, and not discharged outside of the body.

The collagen is a strong coagulant relative to a blood to form a blood clot. Thus, when the body filling agent containing the collagen of the invention is injected into a portion where internal bleeding occurs, the internal bleeding can be stopped by the operation of the collagen. Also, in aneurysm, the body filling agent may be directly injected into a portion projecting from a main blood vessel, i.e. aneurysm, to coagulate the blood in the projected portion.

The body filling agent of the invention may be applied to other portions, not specified in the specification.

While the invention has been explained with reference to the specific embodiments of the invention, the explanation is illustrative and the invention is limited only by the appended claims.

What is claimed is:

1. A body filling material comprising: collagen; and particles containing pericardium, wherein said body-filling material can be deposited in a human subject.

2. A body filling material comprising: collagen; particles of a polymeric material; particles of pericardium; and a liquid, wherein said body-filling material can be deposited in a human subject.

* * * * *